United States Patent
Soultanidis et al.

(10) Patent No.: US 10,059,638 B2
(45) Date of Patent: Aug. 28, 2018

(54) OXYGENATED HYDROCARBON CONVERSION ZONED METHOD

(71) Applicant: ExxonMobil Chemical Patents Inc., Baytown, TX (US)

(72) Inventors: Nikolaos Soultanidis, Houston, TX (US); Jeevan S. Abichandani, Houston, TX (US); Mayank Shekhar, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/555,604

(22) PCT Filed: Dec. 7, 2015

(86) PCT No.: PCT/US2015/064244
§ 371 (c)(1),
(2) Date: Sep. 5, 2017

(87) PCT Pub. No.: WO2016/160081
PCT Pub. Date: Oct. 6, 2016

(65) Prior Publication Data
US 2018/0044260 A1    Feb. 15, 2018

Related U.S. Application Data

(60) Provisional application No. 62/140,566, filed on Mar. 31, 2015.

(51) Int. Cl.
*C07C 1/20* (2006.01)
*C07C 5/41* (2006.01)
*B01J 29/40* (2006.01)
*C07C 5/333* (2006.01)

(52) U.S. Cl.
CPC .............. *C07C 1/20* (2013.01); *B01J 29/405* (2013.01); *C07C 5/333* (2013.01); *C07C 5/415* (2013.01); *B01J 2229/36* (2013.01); *C07C 2529/40* (2013.01)

(58) Field of Classification Search
CPC C07C 1/20; C07C 5/333; C07C 11/02; C07C 2529/40; C07C 5/415; C07C 15/02; C07C 15/08; C07C 2/42; C07C 5/393; B01J 2229/36; B01J 29/405; B01J 37/28
See application file for complete search history.

(56) References Cited

U.S. PATENT DOCUMENTS

| | | |
|---|---|---|
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |
| 3,998,898 A | 12/1976 | Chang et al. |
| 4,016,218 A | 4/1977 | Haag et al. |
| 4,035,430 A | 7/1977 | Dwyer et al. |
| 4,049,573 A | 9/1977 | Kaeding |
| 4,058,576 A | 11/1977 | Chang et al. |
| 4,088,706 A | 5/1978 | Kaeding |
| 4,180,689 A | 12/1979 | Davies et al. |
| 4,347,395 A | 8/1982 | Chu et al. |
| 4,476,338 A | 10/1984 | Chang et al. |
| 4,686,312 A | 8/1987 | Chu et al. |
| 4,935,568 A | 6/1990 | Harandi et al. |
| 5,475,182 A | 12/1995 | Janssen |
| 5,879,655 A | 3/1999 | Miller et al. |
| 5,925,586 A | 7/1999 | Sun |
| 5,925,800 A | 7/1999 | Sun et al. |
| 5,932,512 A | 8/1999 | Sun |
| 5,962,762 A | 10/1999 | Sun et al. |
| 6,005,155 A | 12/1999 | Sun |
| 6,046,373 A | 4/2000 | Sun |
| 6,051,746 A | 4/2000 | Sun et al. |
| 6,153,552 A | 11/2000 | Wachter et al. |
| 6,225,254 B1 | 5/2001 | Janssen et al. |
| 6,372,680 B1 | 4/2002 | Wu et al. |
| 6,448,197 B1 | 9/2002 | Liu et al. |
| 6,521,562 B1 | 2/2003 | Clem et al. |
| 9,035,120 B2 * | 5/2015 | Nesterenko ............... B01J 29/40 585/638 |
| 9,783,460 B2 * | 10/2017 | Ou ............................ C07C 1/22 |
| 2002/0055433 A1 | 5/2002 | Fung et al. |
| 2002/0115897 A1 | 8/2002 | Janssen et al. |
| 2002/0165089 A1 | 11/2002 | Janssen et al. |

(Continued)

FOREIGN PATENT DOCUMENTS

| | | |
|---|---|---|
| CN | 101602643 A | 12/2009 |
| CN | 101602648 A | 12/2009 |

(Continued)

OTHER PUBLICATIONS

Ono, Yoshio et al., Selective Conversion of Methanol into Aromatic Hydrocarbons over Zinc-exchanged ZSM-5 Zeolites, Journal of the Chemical Society, Faraday Transaction 1, vol. 84, No. 4, (1988) pp. 1091-1099.

Inoue, Yoshihiro et al., "Selective conversion of methanol into aromatic hydrocarbons over silver-exchanged ZSM-5 zeolites", Microporous Materials, vol. 4, No. 5, (1995), pp. 379-383.

*Primary Examiner* — Sharon Pregler

(74) *Attorney, Agent, or Firm* — Priya Prasad

(57) ABSTRACT

Processes are provided for conversion of oxygenated hydrocarbon, such as methanol and/or dimethyl ether, to aromatics, such as para-xylene, and olefins, such as ethylene and propylene. The processes entail using a reactor having multiple reaction zones where each zone is prepared to promote desired reactions.

8 Claims, 4 Drawing Sheets

(56) References Cited

U.S. PATENT DOCUMENTS

| | | |
|---|---|---|
| 2015/0175498 A1 | 6/2015 | Ou et al. |
| 2015/0175499 A1 | 6/2015 | Ou et al. |
| 2016/0090332 A1 | 3/2016 | Buchanan et al. |
| 2017/0305810 A1 | 10/2017 | Buchanan et al. |

FOREIGN PATENT DOCUMENTS

| | | |
|---|---|---|
| CN | 101607864 A | 12/2009 |
| CN | 101780417 A | 7/2010 |
| EP | 0424154 A1 | 4/1991 |
| WO | 98/15496 | 4/1998 |
| WO | 01/25151 A1 | 4/2001 |
| WO | 01/36329 A1 | 5/2001 |
| WO | 01/60746 A1 | 8/2001 |
| WO | 03/020667 A1 | 3/2003 |
| WO | 2009/156435 | 12/2009 |
| WO | 2015/094697 A1 | 6/2015 |

* cited by examiner

OXYGENATED HYDROCARBON CONVERSION ZONED METHOD

PRIORITY

This application is a National Phase Application of and claims priority to PCT Application Serial No. PCT/US2015/064244 filed Dec. 7, 2015, which further claims priority to U.S. Provisional Patent Application Ser. No. 62/140,566, filed Mar. 31, 2015, the entire contents of each being incorporated herein by reference.

FIELD

The invention relates to processes for converting oxygenated hydrocarbons, such as methanol, to aromatic and olefinic hydrocarbons.

BACKGROUND OF THE INVENTION

Conversion of oxygenated hydrocarbon, such as methanol, to olefins and other unsaturated compounds is a commonly used reaction scheme for chemical manufacture. Conventional methods can involve exposing an oxygenated hydrocarbon feed to a molecular sieve, such as ZSM-5. In addition to forming olefins, some desirable aromatic compounds can also be formed, such as para-xylene.

U.S. Pat. Nos. 4,049,573 and 4,088,706 disclose conversion of methanol to a hydrocarbon mixture rich in $C_2$-$C_3$ olefins and mononuclear aromatics, particularly p-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

Methanol can be converted to gasoline employing the methanol to gasoline ("MTG") process. The MTG process is disclosed in the patent art, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}$+ olefin precursors of the desired distillate are rapidly converted via hydrogen transfer to heavy polymethylaromatics and $C_4$ to $C_8$ isoparaffins under methanol conversion conditions. The above-identified disclosures are incorporated herein by reference.

Chinese publications CN 101602648, CN 101602643, CN 101607864, and CN 101780417 describe use of selectivated catalysts for conversion of methanol to para-xylene. In these publications, zeolite catalysts are treated with silicate compounds, such as tetraethylorthosilicate, to provide improved selectivity for formation of olefins and para-xylene from methanol feeds. However, silicon treatment introduces several undesired effects, it reduces the per pass aromatic yield and promotes coke deposition that limits the catalyst cycle length. Especially for metal promoted zeolites, silicon treatment can promote metal migration and sintering that results in shorter catalyst lifetime.

The methanol to paraxylene and olefins process ("M2PXO") is a new technology that produces olefins and aromatics at high yields from oxygenated hydrocarbon feeds such as methanol. Provisional U.S. Patent Publication No. 2015/0175498, incorporated here in entirety by reference, describes processes utilizing a catalyst comprising at least one molecular sieve and at least one element selected from Groups 2-12 of the Periodic Table of the Elements. U.S. Patent Publication No. 2015/0175499, incorporated here by reference in its entirety, describes improved aromatics and olefins yield by preparation of molecular sieve (zeolite) catalysts combined with effective conversion conditions. Preparations include modification of the catalyst with a transition metal, steaming of the catalyst, and/or modification of the catalyst with phosphorous.

Despite these advances, the M2PXO process consists of multiple reactions having competitive kinetics including undesired reactions such as methanol decomposition to water and carbon monoxide, alkylation of aromatics with methanol to create undesired aromatics have 9 or more carbon atoms, and other undesired reactions producing coke, methane, carbon monoxide, and carbon dioxide. These competitive kinetics and undesired reactions present a barrier to further maximizing the aromatics selectivity when produced from oxygenated hydrocarbon feeds. There is an ongoing need to provide improved methods for producing aromatics from oxygenated feeds.

SUMMARY

The present invention addresses this need by providing methods for improving the yield of aromatics from conversion of oxygenated hydrocarbon feed, for example, methanol, using a reactor having multiple zones. It has been discovered that the competitive kinetics of the various reactions involved in the conversion process are exploited by preparing each zone to promote one reaction over another in a surprisingly advantageous sequence. Doing so results in improved yield of aromatics and olefins generally; improved yield of desired aromatics and olefins, such as para-xylene, ethylene, and/or propylene; reduced production of less desirable side products, such as methane, CO, $CO_2$, $C_{9+}$ aromatics, and/or coke; or a combination thereof.

Such an oxygenated hydrocarbon conversion process comprises several steps. First, react an oxygenated hydrocarbon feed with a first catalyst in a first zone of a reactor to produce a first mixture comprising olefins, paraffins, and aromatics. Second, react the first mixture with a second catalyst in a second zone of the reactor to convert at least a portion of the first mixture's olefins to aromatics and produce a second mixture comprising olefins, paraffins, and aromatics. The aromatics weight concentration in the second mixture is greater than the aromatics weight concentration in the first mixture. The first and second catalysts comprise at least one molecular sieve and at least one transition metal element selected from groups 2-14 of the Periodic Table. Finally, conduct the second mixture away as reactor effluent.

An oxygenated hydrocarbon conversion process may also comprise the following steps. First, react an oxygenated hydrocarbon feed with a first catalyst in a first zone of a reactor to produce a first mixture comprising olefins, paraffins, and aromatics. Second, react the first mixture with a second catalyst in a second zone of the reactor to convert at least a portion of the first mixture's olefins to aromatics and produce a second mixture comprising olefins, paraffins, and aromatics. The aromatics weight concentration in the second mixture is greater than the aromatics weight concentration in the first mixture. The first and second catalysts comprise at least one molecular sieve and at least one transition metal element selected from groups 2-14 of the Periodic Table. Third, react the second mixture with a third catalyst in a third zone of the reactor to convert at least a portion of the second mixture's paraffins to unsaturated hydrocarbons and produce a third mixture comprising olefins, paraffins, and aromatics. The third catalyst comprises at least one molecular sieve and at least one element selected from groups 2-14 of the Periodic Table. Finally, conduct the third mixture away as reactor effluent.

DESCRIPTION

Figure 1:
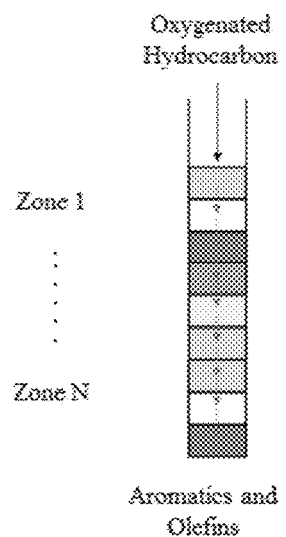
FIG. 1 depicts a general configuration of a reactor having N zones.

The present invention provides methods for improving the yield of aromatics from conversion of oxygenated hydrocarbon feed, for example, methanol, using a reactor having multiple zones. For purposes of this application, the term "zone", refers to a location within a reactor wherein a desired reaction is carried out. For example, a "paraffin dehydrogenation zone" is a location within a reactor for conducting paraffin dehydrogenation reactions.

The main reactions occurring during conversion of oxygenated hydrocarbon feed to aromatics and olefins are a) the hydrocarbon pool mechanism, b) olefin dehydrocyclization, c) paraffin dehydrogenation, d) methanol decomposition, and e) aromatics alkylation by methanol. The hydrocarbon pool reactions initially begin by dehydration of oxygenated hydrocarbon such as methanol to the corresponding ether (dimethyl ether for methanol) among other initial species. These initial species build up within catalyst pores to form a hydrocarbon pool. The species within the hydrocarbon pool continually react with additional oxygenated hydrocarbon feed (or the corresponding ether) to form olefins, paraffins, some aromatics, and undesired coke. Olefin dehydrocyclization involves both dehydrogenation and cyclization of non-cyclic hydrocarbon to produce a hydrocarbon having at least one cyclic structure. The cyclic structures can be saturated or unsaturated, with unsaturated structures including aromatic structures. Paraffin dehydrogenation refers to removal of hydrogen from a paraffin to form unsaturated hydrocarbon, for example, olefins. Methanol decomposition is the undesired conversion of methanol to water and carbon monoxide. Aromatic alkylation by methanol refers to the addition of alkyl groups such as methyl alcohol (or methanol) to aromatic ring molecules. While alkylation of benzene and toluene to xylenes is desired, alkylation of xylenes and higher $C_{9+}$ aromatics is not. Therefore, aromatic alkylation reactions are undesired where xylenes or $C_{9+}$ aromatics are present. $C_{9+}$ aromatics are molecules containing 9 or more carbon atoms including a benzene ring.

The competitive kinetics of these reactions may be exploited by a method utilizing a reactor having multiple zones, where each zone is designed to promote one reaction over another. Favoring one or more desired oxygenated hydrocarbon conversion to aromatics reaction(s) over another in sequential zones can allow for improved yield of aromatics and olefins generally; improved yield of desired aromatics and olefins, such as para-xylene, ethylene, and/or propylene; reduced production of less desirable side products, such as methane, CO, $CO_2$, $C_{9+}$ aromatics, and/or coke; or a combination thereof.

It has been discovered that a method of reacting an oxygenated hydrocarbon in a reactor having at least a first zone that promotes MTG reactions and a second zone that promotes olefin dehydrocyclization reactions increases aromatic and olefin yields and decreases undesired side products. Without being bound by any theory, it is believed that favoring the MTG reactions in a first zone consumes the methanol and reduces the amount of methanol decomposition that can occur when methanol is present in a reaction zone that promotes olefin dehydrocyclization. It is further believed that by avoiding methanol decomposition, more methanol (or other oxygenated hydrocarbon feed) is available for conversion to aromatics and olefins. Additionally, it is believed that favoring production of hydrocarbon pool reaction products from methanol in a first zone reduces the amount of methanol available in subsequent zone(s) for aromatic alkylation to form undesired $C_{9+}$ aromatics.

Accordingly, suitable reactors can have at least 2, at least 3, or at least 4 zones. Generally, FIG. 1 illustrates a reactor having N zones. A reactor can have at least a hydrocarbon pool zone and an olefin dehydrocyclization zone, respectively. A reactor may have a hydrocarbon pool zone to promote conversion of oxygenated hydrocarbon, such as methanol, to olefins, aromatics, and paraffins with minimum methanol decomposition to carbon monoxide. Additionally, the reactor may have an olefin dehydrocyclization zone to promote conversion of the olefins produced in the hydrocarbon pool zone to aromatics. Optionally, the reactor can have a paraffin dehydrogenation zone to promote conversion of unreacted paraffins to unsaturated hydrocarbon. For example, a reactor can have at least a hydrocarbon pool zone, an olefin dehydrocyclization zone, and a paraffin dehydrogenation zone, respectively.

A reactor having at least a hydrocarbon pool zone followed by an olefin dehydrocyclization zone can have ≥3 wt %, e.g., ≥5 wt %, ≥7 wt %, or ≥10 wt % more aromatics in the reactor's hydrocarbon effluent than a single-zone reactor operated under similar conditions. A reactor having at least a hydrocarbon pool zone followed by an olefin dehydrocyclization zone can have ≥50 wt %, e.g., ≥53 wt %, ≥55 wt %, or ≥60 wt % aromatics in the reactor's effluent, based on the weight of the effluent. A reactor having at least a hydrocarbon pool zone followed by an olefin dehydrocyclization zone can have ≥5 wt %, e.g., ≥10 wt %, ≥15 wt %, or ≥20 wt % less coke produced than a single-zone reactor operated under similar conditions. A reactor having at least a hydrocarbon pool zone followed by an olefin dehydrocyclization zone can have ≥3 wt %, e.g., ≥5 wt %, ≥7 wt %, or ≥10 wt % less methane, carbon monoxide, or carbon dioxide in the reactor's hydrocarbon effluent than a single-zone reactor operated under similar conditions. A reactor having at least a hydrocarbon pool zone followed by an olefin dehydrocyclization zone can have i) ≥3 wt %, e.g., ≥5 wt %, ≥7 wt %, or ≥10 wt % more benzene, toluene, and/or xylene aromatics and ii) ≥1 wt %, e.g., ≥3 wt %, ≥5 wt %, or ≥7 wt % less $C_{9+}$ aromatics in the reactor's effluent than a single-zone reactor operated under similar conditions.

Promoting a particular reaction in each zone may be accomplished by adjusting conditions in each zone such as temperature, catalyst, catalyst preparation, or any combination thereof. Adjusting catalyst can include selecting different zeolite known to promote the desired reaction for each zone. The preparation of the catalyst can include modification of the catalyst with a transition metal, such as Zn, Ga, or Ag. The preparation of the catalyst can also include steaming of the catalyst. In some aspects, the preparation of the catalyst can further include modifying the catalyst with phosphorous.

Preparation of the catalyst may include modification of a molecular sieve or zeolite catalyst with a transition metal, such as Zn, Ga, or Ag. Additionally, the catalyst preparation may include modification of amounts and/or ratio of primary transition metal and secondary transition metal. It has been discovered that modifying a molecular sieve or zeolite catalyst with a transition metal, such as Zn, Ga, or Ag, can increase production of aromatics. Without being bound by any theory, it is believed that modifying with transition metals on the catalyst promote olefin dehydrocyclization reactions because of introduction of a dehydrogenation function that removes hydrogen in the form of $H_2$. It has further been discovered that modifying with transition metals on the catalyst also promote undesired methanol decomposition reactions.

A molecular sieve or zeolite catalyst modified with a transition metal can be steamed under effective steaming conditions. Steaming of a catalyst can have various impacts on the catalyst. Steaming a catalyst has an impact similar to aging of the catalyst, so that changes in catalyst activity that occur early during a processing run can be reduced or minimized. This includes reducing or minimizing the initial cracking activity of a catalyst. Without being bound by any particular theory, it is believed that steaming of metal-modified conversion catalysts can improve the dispersion of the modifying metals on the catalyst. Additionally, when a conversion catalyst is newly synthesized or "fresh", the catalyst may have a relatively high cracking activity due to the presence of additional acidic sites on the catalyst. Steaming the catalyst for a period of time, prior to use in a conversion reaction, can reduce the number of acidic sites. This improved dispersion and reduced acidity favors hydrocarbon pool reactions and reduces the loss of oxygenated hydrocarbon feed to formation of side products, such as carbon oxides or coke.

Preparation of the catalyst may further include modifying a steamed, metal-modified catalyst with phosphorous. In some aspects, in addition to providing an improved yield of aromatics, modifying a catalyst with phosphorous can also improve the stability of a catalyst over time during a processing run.

Accordingly, a reactor may comprise at least a first zone (a hydrocarbon pool zone) with a first catalyst and second zone (an olefin dehydrocyclization zone) with a second catalyst. Preferably, the first catalyst comprises a steamed, metal-modified catalyst with phosphorus and the second catalyst comprises a fresh or un-steamed catalyst. More preferably, the first catalyst comprises a steamed, metal-modified catalyst with phosphorus and the second catalyst comprises a fresh or un-steamed metal-modified catalyst.

Alternatively or in addition to the above preparations, a reactor may have multiple zones operating at different temperatures that favor a particular reaction. Higher temperatures are believed to increase the yield of aromatics but also increase the yield of undesirable side products, such as carbon oxides or coke and decrease catalyst stability. Without being bound by any theory, the undesirable side products are believed to form in part by methanol decomposition reactions. Accordingly, a reactor may comprise at least a first zone operating at a temperature from 300° C. to 450° C. and a second zone operating at a temperature from 400° C. to 550° C. Optionally, a reactor may further comprise a third zone operating at a temperature greater than 500° C. to promote further unsaturated hydrocarbon production reactions.

A reactor can have a combination of the above conditions to promote a particular reaction in each zone and improve the olefins and aromatics yield. A reactor may comprise at least a first zone with a first catalyst operating at a temperature from 300° C. to 450° C. and a second zone with a second catalyst operating at a temperature from 400° C. to 550° C. where the first catalyst comprises a steamed, metal-modified catalyst with phosphorus and the second catalyst comprises a fresh or un-steamed catalyst.

It has been further discovered that increasing the amount of transition metal used to modify the second zone catalyst further increases the aromatic production while maintaining the benefit of reduced methane, coke, CO, $CO_2$, and $C_{9+}$ aromatics production afforded by the zoned reactor approach. A reactor having at least >1 wt % more concentration of transition metal in the second zone catalyst than in the first zone catalyst can have ≥3 wt %, e.g., ≥5 wt %, ≥7 wt %, or ≥10 wt % more aromatics in the reactor's effluent than a reactor having the same amount of transition metal in the catalyst of first and second zones operated under similar conditions. It is believed the metal component of these catalysts promotes both undesired methanol decomposition and desired olefin dehydrocyclization. Advantageously, methanol is converted via the hydrocarbon pool reactions of the first zone reducing the amount of methanol available for methanol decomposition in the second zone. The first zone is modified with lower amounts of transition metal than in the second or later zones. Further, using higher amounts of transition metal in the second zone catalyst, after the methanol has been converted to desired intermediate hydrocarbon pool products, allows increased aromatic formation via dehydrocyclization reactions.

Accordingly, a reactor may comprise at least a first zone (a hydrocarbon pool zone) with a first catalyst and second zone (an olefin dehydrocyclization zone) with a second catalyst. The first catalyst may be modified with 0 to 5 wt % transition metal. The second catalyst may be modified with 1 to 20 wt %. Preferably, the first catalyst comprises a steamed, metal-modified catalyst with phosphorus and the second catalyst comprises a fresh (unsteamed) metal-modified catalyst with phosphorus where the second catalyst has ≥2 wt %, e.g., ≥4 wt %, ≥6 wt %, ≥10 wt %, ≥15 wt %, or up to 20 wt % more transition metal than the first catalyst. Optionally, the second catalyst comprises a steamed, metal-modified catalyst with phosphorus where the second catalyst has ≥2 wt %, e.g., ≥4 wt %, ≥6 wt %, ≥10 wt %, ≥15 wt %, or up to 20 wt % more transition metal than the first catalyst.

The above descriptions are not intended to preclude other combinations of conditions, catalyst, and/or catalyst preparation that provide at least a first zone that promotes olefin and aromatic production over formation of carbon oxides and coke from oxygenated hydrocarbon, and at least a second zone that promotes dehydrocyclization to form even more aromatics.

Catalysts

The catalyst used herein comprises a molecular sieve and a Group 2-14 element, preferably a Group 8-14 element, or a molecular sieve and a combination of metals from the same group of the Periodic Table. Suitable catalysts are described in Provisional U.S. Patent Publication Nos. 2015/0175498 and 2015/0175499, which are both incorporated here in entirety by reference. The catalyst can optionally further comprise phosphorus and/or lanthanum and/or other elements from Group 1-2 and/or Group 13-16 of the Periodic Table that provide structural stabilization. In this sense, the term "comprising" can also mean that the catalyst can comprise the physical or chemical reaction product of the molecular sieve and the Group 2-14 element or combination of elements from the same group (and optionally phosphorus and/or lanthanum and/or other elements from groups 1-2 and/or group 13-16). In this description, reference to a group number for an element corresponds to the current IUPAC numbering scheme for the periodic table. Optionally, the catalyst may also include a filler or binder and may be combined with a carrier to form slurry.

A catalyst comprising a molecular sieve can be modified by the Group 2-14 metal(s) in any convenient manner Typical methods for modifying a catalyst with a metal include impregnation (such as by incipient wetness), ion exchange, deposition by precipitation, and any other convenient method for depositing a metal that is supported by a catalyst and/or a catalyst support.

In various aspects, the molecular sieve comprises ≥10.0 wt % of the catalyst. The upper limit on the amount of molecular sieve in the catalyst may be from 10.0 wt % to 100.0 wt %. The lower limit on the amount of molecular sieve in the catalyst may be from 10.0 wt % to 100.0 wt %.

As used herein the term "molecular sieve" refers to crystalline or non-crystalline materials having a porous structure. Microporous molecular sieves typically have pores having a diameter of ≤about 2.0 nm. Mesoporous molecular sieves typically have pores with diameters of about 2 to about 50 nm. Macroporous molecular sieves have pore diameters of >50.0 nm. The upper limit on the pore diameter may be from $1.00 \times 10^4$ nm to 5.0 nm. The lower limit on the pore diameter may be from $5.00 \times 10^3$ nm to 1.0 nm or less.

Additionally or alternatively, some molecular sieves useful herein are described by a Constraint Index of about 1 to about 12. The upper limit on the range of the Constraint Index may be from 12.0 to 2.0. The lower limit on the range of the Constraint Index may be from 11.0 to 1.0. Constraint Index is determined as described in U.S. Pat. No. 4,016,218, incorporated herein by reference for details of the method.

Particular molecular sieves are zeolitic materials. Zeolitic materials are crystalline or para-crystalline materials. Some zeolites are aluminosilicates comprising [$SiO_4$] and [$AlO_4$] units. Other zeolites are aluminophosphates (AlPO) having structures comprising [$AlO_4$] and [$PO_4$] units. Still other zeolites are silicoaluminophosphates (SAPO) comprising [$SiO_4$], [$AlO_4$], and [$PO_4$] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 10 to 200, preferably about 10 to 80, more preferably about 20 to 60, and most preferably about 30 to 55.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Patent No. 3,832,449); ZSM-22 (U.S. Pat. No. 4,556,477); ZSM-23 (U.S. Pat. No. 4,076,842); ZSM-34 (U.S. Pat. No. 4,079,095); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZK5, erionite, and chabazite.

Another option for characterizing a zeolite (or other molecular sieve) is based on the nature of the ring channels in the zeolite. The ring channels in a zeolite can be defined based on the number of atoms including in the ring structure that forms the channel. In some aspects, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, PON, SFG, STF, STI, TON, TUN, MRE, and PON.

The catalyst also includes at least one metal selected from Group 2-14, preferably Group 8-14, of the Periodic Table, such as at least two metals (i.e., bimetallic) or at least three metals (i.e., trimetallic). Typically, the total weight of the Group 2-14 elements is ≥0.1wt % based on the total weight of the catalyst. Typically, the total weight of the Group 2-14 element is ≤about 20.0 wt %, based on the total weight of the catalyst. Thus, the upper limit on the range of the amount of the Group 2-14 elements added to the molecular sieve may be from 20.0 wt % to 0.1 wt %. The lower limit on the range of the amount of the Group 2-14 elements added to the molecular sieve may be from 20.0 wt % to 0.1 wt %. Of course, the total weight of the Group 2-14 elements shall not include amounts attributable to the molecular sieve itself.

Additionally or alternatively, in some aspects, the catalyst can also include at least one of phosphorous and/or lanthanum and/or other elements from groups 1-2 and/or group 13-16, such as at least two such elements or at least three such elements. Typically, the total weight of the phosphorous and/or lanthanum and/or other elements from groups 1-2 and/or groups 13-16 is ≥0.1 wt % based on the total weight of the catalyst. Typically, the total weight of the phosphorous and/or lanthanum and/or other elements from groups 1-2 and/or groups 13-16 is ≤ about 10.0 wt %, based on the total weight of the catalyst. Thus, the upper limit on the range of the phosphorous and/or lanthanum and/or other elements from groups 1-2 and/or groups 13-16 added to the molecular sieve may be from 10.0 wt % to 0.1 wt %; and the lower limit on the range added to the molecular sieve may be from 10.0 wt % to 0.1 wt %. Of course, the total weight of the phosphorous and/or lanthanum and/or other elements from Groups 1-2 and/or Groups 13-16 shall not include amounts attributable to the molecular sieve itself.

For the purposes of this description and claims, the numbering scheme for the Periodic Table Groups corresponds to the current IUPAC numbering scheme. Therefore, a "Group 4 metal" is an element from Group 4 of the Periodic Table, e.g., Hf, Ti, or Zr. The more preferred molecular sieves are SAPO molecular sieves, and metal-substituted SAPO molecular sieves. In particular embodiments, one or more Group 1 elements (e.g., Li, Na, K, Rb, Cs, Fr) and/or Group 2 elements (e.g., Be, Mg, Ca, Sr, Ba, and Ra) and/or phosphorous and/or Lanthanum may be used. One or more Group 7-9 element (e.g., Mn, Tc, Re, Fe, Ru, Os, Co, Rh, and Ir) may also be used. Group 10 elements (Ni, Pd, and Pt) are less commonly used in applications for forming olefins and aromatics, as the combination of a Group 10 element in the presence of hydrogen can tend to result in saturation of aromatics and/or olefins. In some embodiments, one or more Group 11 and/or Group 12 elements (e.g., Cu, Ag, Au, Zn, and Cd) may be used. In still other embodiments, one or more Group 13 elements (B, Al, Ga, In, and Tl) and/or Group 14 elements (Si, Ge, Sn, Pb) may be used. In a preferred embodiment, the metal is selected from the group consisting of Zn, Ga, Cd, Ag, Cu, P, La, or combinations thereof. In another preferred embodiment, the metal is Zn, Ga, Ag, or a combination thereof.

Particular molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (E1APSO where E1 is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, *Handbook of Molecular Sieves*, Van Nostrand Reinhold, New York, N.Y. (1992), which is herein fully incorporated by reference.

In some aspects, the catalyst comprises a molecular sieve as modified by the Group 2-14 element, preferably by the Group 8-14 element, and/or a Group 1-2, Group 13-16, lanthanum, and/or phosphorous is a ZSM-5 based molecular sieve. In some preferred aspects, the Group 2-14 element can be selected from Groups 11-13, such as Zn, Ga, Ag, or combinations thereof. In other aspects, the Group 2-14 element can be two or more elements from Groups 11-13, such as two or more elements from the same group in Groups 11-13. In still other aspects, the molecular sieve can be modified with at least one element from Groups 2-14, such as at least two elements or at least three elements from Groups 2-14, the at least two elements or at least three elements optionally being from the same group in Groups 2-14. In any of the above aspects, a catalyst comprising a molecular sieve can be further modified by an element from Groups 1-2, Groups 13-16, lanthanum, and/or phosphorus.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

Prior to using a catalyst for conversion of oxygenated hydrocarbon to aromatics and olefins, the catalyst can be steamed under effective steaming conditions. General examples of effective steaming conditions including exposing a catalyst to an atmosphere comprising steam at a temperature of about 400° C. to about 850° C., or about 400° C. to about 750° C., or about 400° C. to about 650° C., or about 500° C. to about 850° C., or about 500° C. to about 750° C., or about 500° C. to about 650° C. The atmosphere can include as little as 1 vol % water and up to 100 vol % water. The catalyst can be exposed to the steam for any convenient period of time, such as about 10 minutes (0.15 hours) to about 48 hours. In some aspects, the time for exposure of the catalyst to steam is at least about 0.25 hours, such as about 0.25 hours to about 8 hours, or about 0.25 hours to about 4 hours, or about 0.25 hours to about 2 hours, or about 0.5 hours to about 8 hours, or about 0.5 hours to about 4 hours, or about 0.5 hours to about 2 hours, or about 1 hour to about 8 hours, or about 1 hour to about 4 hours, or about 1 hour to about 2 hours.

Conversion Process

A process for conversion of oxygenated hydrocarbon feed to aromatics and olefins in a reactor having multiple zones will now be described. The oxygenated hydrocarbon feed can comprise aliphatic aldehydes, carboxylic acids, carbohydrates, alcohols, ethers, acetals and analogs. Preferably, the oxygenated hydrocarbon feed comprises any monohydric alcohol having from 1 to 4 carbon atoms or ethers derived from these alcohols. Thus, methanol, ethanol, n-propanol, isopropanol, n-butanol, sec-butanol and isobutanol may be used either alone or in admixture with ethers derived from such alcohols. Likewise, the noted ethers, e.g., methylethyl ether may be similarly used. Particularly preferred feeds are methanol, dimethyl ether and mixtures thereof. Optionally, the oxygenated hydrocarbon feed also contains $C_1$-$C_5$ alkanes, such as methane and/or propane, for conversion of at least a portion of the alkanes and the majority of oxygenated hydrocarbon to aromatics. Additionally or alternately, the feed can be diluted with steam at any convenient time, such as prior to entering a conversion reactor or after entering a conversion reactor. Examples of preferable feeds (excluding any optional dilution with steam) include feeds that are substantially methanol, feeds that are substantially dimethyl ether, feeds that are substantially methanol and dimethyl ether, or feeds that include at least about 50 wt % of methanol and/or dimethyl ether, such as at least about 60 wt % or at least about 70 wt %. A feed that is substantially composed of a compound (or compounds) is a feed that is at least 90% wt % of the compound (or compounds), or at least 95 wt % of the compound, or at least 98 wt % of the compound, or at least 99 wt % of the compound. For a feed that is less than 100 wt % methanol and/or dimethyl ether (excluding any optional dilution with steam), other hydrocarbon compounds (and/or hydrocarbonaceous compounds) in the feed can include paraffins, olefins, aromatics, and mixtures thereof.

The feed can be exposed to the conversion catalyst in any convenient type of reactor which may be configured with the zones described above promoting particular reactions in each zone. Suitable reactor configurations include fixed bed reactors, fluidized bed reactors (such as ebullating bed reactors), riser reactors, moving-bed reactors, and other types of reactors where the feed can be exposed to the catalyst in a controlled manner Preferable reactor configuration is a fixed bed reactor having at least 2, at least 3, or at least 4 reaction zones.

An oxygenated hydrocarbon feed can be converted to aromatics (including para-xylene) and olefins by exposing the feed to a conversion catalyst under effective conversion conditions. General conversion conditions for conversion of oxygenated hyrdocarbon to aromatics and olefins include a pressure of about 100 kPaa (kilopascals absolute) to about 2500 kPaa, or about 100 kPaa to about 2000 kPaa, or about 100 kPaa to about 1500 kPaa, or about 100 kPaa to about 1200 kPaa. The amount of feed (weight) relative to the amount of catalyst (weight) can be expressed as a weight hourly space velocity (WHSV). Suitable weight hourly space velocities include a WHSV of about 0.1 $hr^{-1}$ to about 20 $hr^{-1}$, or about 1.0 $hr^{-1}$ to about 10 $hr^{-1}$.

Generally, the temperature for the conversion reaction can vary depending on the nature of the catalyst used for the conversion. Suitable reaction temperatures include a temperature of about 300° C. to about 600° C., or about 400° C. to about 600° C., or about 400° C. to about 575° C., or about 425° C. to about 600° C., or about 425° C. to about 575° C., or about 450° C. to about 600° C., or about 450° C. to about 575° C., or about 475° C. to about 600° C., or about 475° C. to about 575° C., or about 500° C. to about 600° C., or about 500° C. to about 575° C., or about 525° C. to about 575° C.

Figure 2:
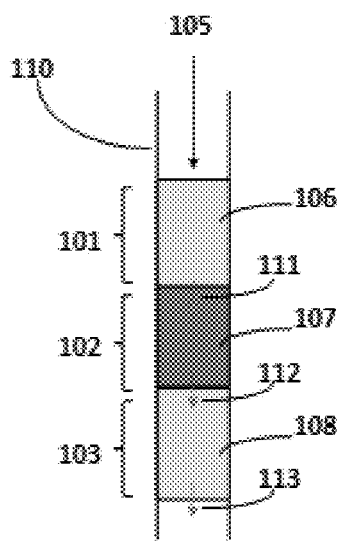
FIG. 2 illustrates a zoned oxygenated hydrocarbon conversion process.

Referring to FIG. 2 which illustrates a conversion process, an oxygenated hydrocarbon feed 105 can be introduced into a reactor 110 having at least 2 zones containing conversion catalyst. Steam (not shown) can optionally also be introduced into the reactor 110 with the oxygenated hydrocarbon feed 105. The oxygenated hydrocarbon feed 105 is reacted with a first catalyst 106 in the first zone 101 of reactor 110. The conditions in the first zone 101 are adjusted to promote methanol to gasoline reactions to produce a first mixture 111 comprising olefins, paraffins, and aromatics. The first mixture 111 is then reacted with a second catalyst 107 in the second zone 102 of the reactor to promote olefin dehydrocyclization reactions converting at least a portion of the first mixture's olefins to aromatics and producing a second mixture 112 comprising olefins, paraffins, and aromatics. The aromatics weight percent of the second mixture is greater than the aromatics weight percent of the first mixture.

Optionally, the second mixture 112 may be reacted with a third catalyst 108 in a third zone 103 of the reactor 110 to convert at least a portion of the second mixture's paraffins to unsaturated hydrocarbon and produce a third mixture 113 comprising olefins, paraffins, and aromatics. The olefins plus aromatics weight percent of the third mixture is greater than the olefins plus aromatics weight percent in the second mixture.

A reactor effluent 115 comprising the second mixture 112 if the reactor has two zones, the third mixture 113 if the reactor has three zones, or the $N^{th}$ mixture if the reactor has N zones is conducted away for separation into desired products.

Figure 3:
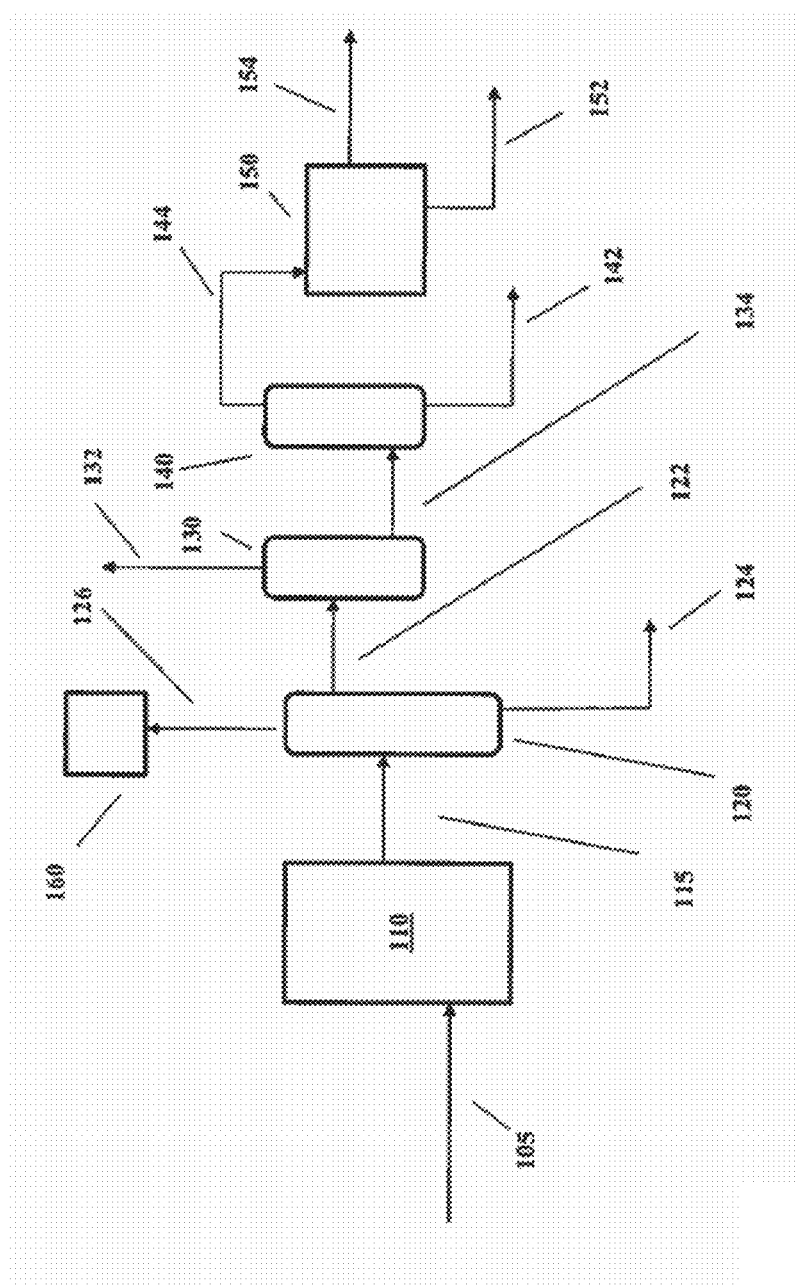
FIG. 3 describes further separation as part of a zoned oxygenated hydrocarbon conversion process.

Referring now to FIG. 3 where like elements have like numbers, after performing the conversion reactions, the reactor effluent 115 can be quenched in quench stage 120 to facilitate separation of the effluent based on phases of the effluent. The quench can be sufficient to allow removal of water 124 from the effluent as a liquid. Light organics containing 4 carbons or less are removed as a light ends gas phase stream 126. Ethylene and propylene can subsequently be separated from this light ends stream 126 in one or more recovery processes 160. The remaining portion of the effluent 115 can substantially correspond to hydrocarbons that are liquids 122 at standard temperature and pressure. A series of separations can then be performed to separate out desired products. For example, a first separation stage 130 on the liquid effluent 122 can separate $C_{7-}$ (lower boiling) compounds 132 from $C_{8+}$ (higher boiling) compounds 134. In the first separation 130, para-xylene and other $C_{8+}$ molecules are included in the higher boiling fraction 134, while $C_{7-}$ compounds (benzene, toluene) and other lower boiling compounds such as oxygenates form the lower boiling fraction 132. In this discussion, a $C_{7-}$ product stream 132 is defined as a product stream where at least 50 wt % of the hydrocarbons correspond to hydrocarbons having 7 carbons or less. Similarly, a $C_{8+}$ product stream 134 is defined as a product stream where at least 50 wt % of the hydrocarbons correspond to hydrocarbons having at least 8 carbons. This lower boiling fraction 132 may also contain a variety of non-aromatic compounds.

The $C_{8+}$ fraction 134 can then be further separated in a second separation stage 140 into a $C_8$ fraction 144 and a $C_{9+}$ fraction 142. The $C_{9+}$ fraction 142 will typically be primarily aromatics. In this discussion, a $C_8$ product stream 144 is defined as a product stream where at least 50 wt % of the hydrocarbons correspond to hydrocarbons having 8 carbons. Similarly, a $C_{9+}$ product stream 142 is defined as a product stream where at least 50 wt % of the hydrocarbons correspond to hydrocarbons having at least 9 carbons. In some aspects, if a distillation column is used, the first separation 130 and second separation 140 can be combined to form the $C_{7-}$, $C_8$, and $C_{9+}$ fractions (132, 144, and 142 respectively) in a single distillation or fractionation process. In some aspects, the separations to form the $C_{7-}$, $C_8$, and $C_{9+}$ fractions can correspond to any convenient number of distillation steps in order to improve recovery of the desired $C_8$ fraction.

The $C_8$ fraction 144 of the liquid effluent from conversion will typically include at least a portion of xylene isomers other than para-xylene. The ortho- and meta-xylene isomers 152 can be separated in stage 150 from the para-xylene isomers 154 by any convenient method, such as by using crystallization to separate the isomers or by selective adsorption. Optionally, the $C_8$ fraction 144 can be treated in a xylene isomerization unit (not shown) prior to recovery of the para-xylene 154. This can increase the concentration of para-xylene in the $C_8$ fraction 144 relative to the concentration prior to the xylene isomerization. Optionally, the separated ortho- and meta-xylenes 152 can be recycled back (not shown) to the distillation step(s) for further recovery of any remaining para-xylene and/or for further isomerization to form more para-xylene.

EXAMPLE 1

Figure 4:
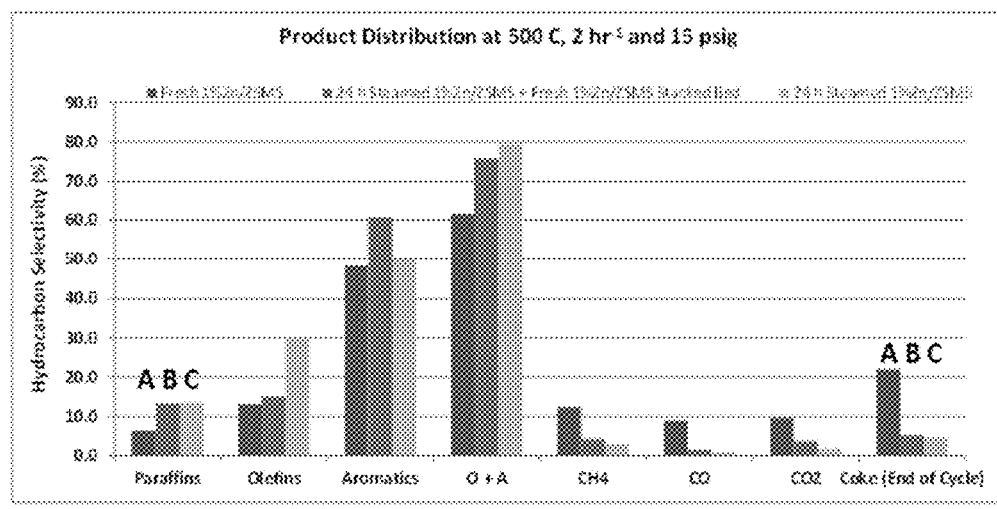
FIGS. 4, 5, and 6 are charts illustrating product distribution for oxygenated hydrocarbon conversion processes.
Figure 5:
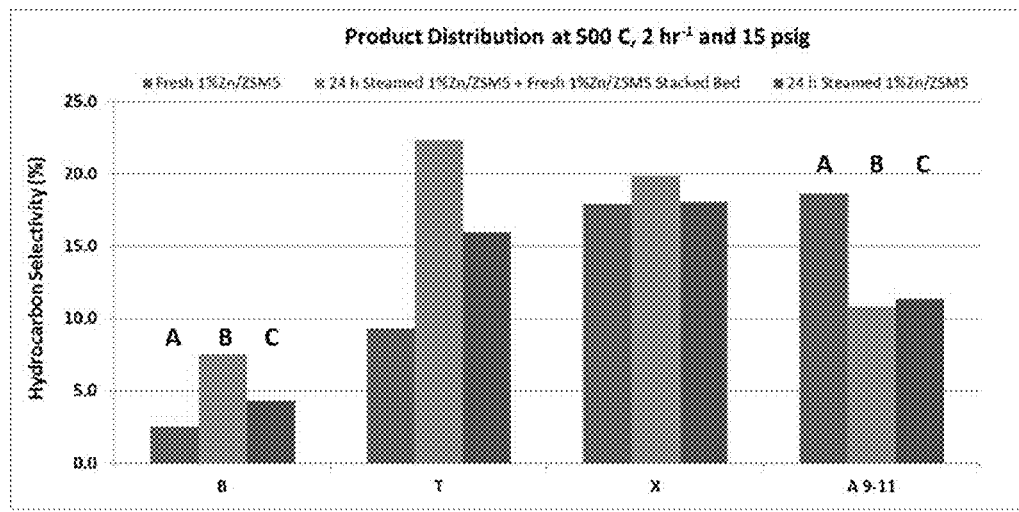

An oxygenated hydrocarbon conversion process was carried out under similar conditions in a single-zoned reactor and in a multi-zoned reactor for comparative purposes. The results are summarized in FIG. 4 and FIG. 5. The conversion reactions were performed to achieve 100% conversion of a methanol feed. The catalyst used for the conversion reactions in FIG. 4 and FIG. 5 was bound ZSM-5 catalyst modified to include 1 wt % Zn. Run A (comparative) in FIG. 4 and FIG. 5 corresponds to a single-zoned reactor containing the as-is or "fresh" catalyst. Run B was a reactor having a first zone with the same ZSM-5 catalyst that was prepared by steaming for 24 hours prior to use in the conversion reaction and a second zone with the same fresh catalyst. Run C (comparative) was a single-zoned reactor containing the same ZSM-5 catalyst steamed for 24 hours. In FIG. 4 and FIG. 5, the results are displayed as a grouping of bar graphs for each product type, with the bars shown in the order A-B-C, as indicated for the first data set (paraffins) and the last data set (coke).

FIG. 4 shows the average product distribution in the conversion reactor effluent for the single and multi-zoned reactors. The conversion reactions for the results in FIG. 4 were performed at 500° C., 15 psig and a weight hourly space velocity (WHSV) of 2 $hr^{-1}$. The fresh catalyst comparative process Run A shows the effect of high acidity and relatively lower metal (Zn) dispersion. The Run A maximum aromatics yield is 48 wt %. Significant concentrations of carbon dioxide ($CO_2$) and carbon monoxide (CO) indicate the severity of the methanol decomposition. The strong acidity effect is reflected in the high methane ($CH_4$) and coking (the scale for the coking columns is ×10 so the Run A coke is actually 2% coke in Run A). The 24 hr steamed catalyst comparative process Run C results in little $CO_2$ and CO produced due to the better metal dispersion. Additionally, Run C a single-zone steamed catalyst produced lower methane and coke with higher olefins as evidence of reduced methanol decomposition due to reduced catalytic acidity. Exemplary Run B includes the steamed catalyst (lower acidity, higher dispersion) in the first zone and the fresh catalyst (higher acidity, lower dispersion) in the second zone. The Run B results show a significant increase in aromatics (61 wt %) with olefin yields similar to the Run A fresh catalyst (more olefins converted to aromatics). The Run B two-zone process effluent had ≥10 wt % more aromatics than the effluent of either single-zone comparative process Run A or Run C when operated at the same conditions. Additionally, the two-zone Run B process produced paraffin, methane, CO, $CO_2$, and coke yields similar to the Run C steamed catalyst (less methanol converted to undesired side products). It is noted that the amount of coke shown in FIG. 4 represents the amount of coke measured on the catalyst after the end of the process run.

FIG. 5 contains the distribution of aromatics produced in the conversion reactor effluent for the single and multi-zoned reactor runs A, B and C summarized above regarding FIG. 4. The results of exemplary Run B indicate an increase in concentration of desired aromatics benzene, toluene, and xylenes and a decrease in concentration of undesired $C_{9+}$ aromatics over single bed comparative reactors in Run A and Run C.

EXAMPLE 2

Figure 6:
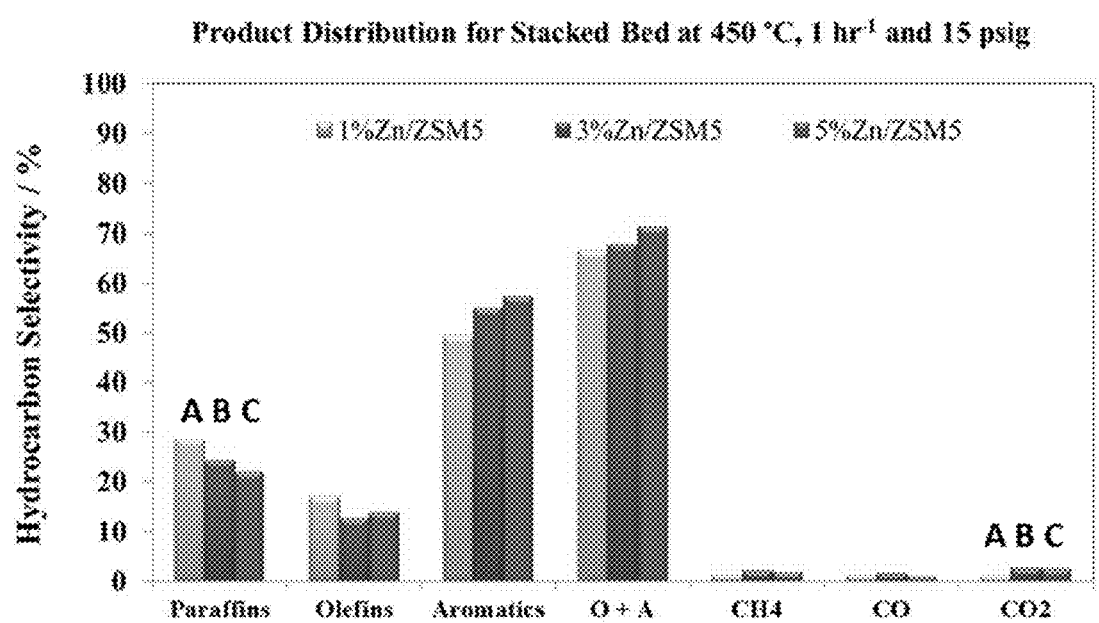

An oxygenated hydrocarbon conversion process was carried out under similar conditions in a multi-zoned reactor. The results are summarized in FIG. 6. The conversion reactions were performed to achieve 100% conversion of a methanol feed. The catalyst used in the first zone of the multi-zoned reactor through all three runs described in FIG. 6 was a bound ZSM-5 catalyst modified to include 1 wt % Zn that was prepared by steaming for 24 hours prior to use in the conversion reaction. The second zone of the reactor contained bound ZSM-5 catalyst that was modified to include increasing amounts of Zn. The second zone catalyst for Run A, Run B, and Run C was modified with 1 wt % Zn, 3 wt % Zn, and 5 wt % Zn respectively. The second zone catalyst was also prepared by steaming for 24 hours prior to use in conversion reaction. In FIG. 6, the results are displayed as a grouping of bar graphs for each product type, with the bars shown in the order A-B-C, as indicated for the first data set (paraffins) and the last data set ($CO_2$).

FIG. 6 contains the average product distribution in the conversion reactor effluent for the multi-zoned reactor. The conversion reactions for the results in FIG. 6 were performed at 450° C., 15 psig and a weight hourly space velocity (WHSV) of 1 $hr^{-1}$. The aromatics concentration in the reactor effluent increased with increased Zn content in the second zone catalyst. Run C (5 wt % Zn in the second zone catalyst) had increased aromatics concentration by 8 wt % over Run A (1 wt % Zn in the second zone catalyst). Additionally, undesired reaction product concentrations for methane ($CH_4$), carbon monoxide (CO), and carbon dioxide ($CO_2$) remained low at less than 3 wt %. Further, lower paraffin concentration was observed in Run B and Run C effluent compared to Run A with Run C having 6 wt % less paraffin concentration than Run A.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:

1. An oxygenated hydrocarbon conversion process, comprising:
   a) reacting an oxygenated hydrocarbon feed with a first catalyst in a first zone of a reactor to produce a first mixture comprising olefins, paraffins, and aromatics; and
   b) reacting the first mixture with a second catalyst in a second zone of the reactor to convert at least a portion of the olefins in the first mixture to aromatics and produce a second mixture comprising olefins, paraffins, and aromatics;
   wherein, the aromatics weight concentration in the second mixture is greater than the aromatics weight concentration in the first mixture and the first and second catalysts comprise at least one molecular sieve and at least one transition metal element selected from groups 2-14 of the Periodic Table;

c) reacting the second mixture from step b) with a third catalyst in a third zone of the reactor to convert at least a portion of the paraffins in the second mixture to unsaturated hydrocarbons and produce a third mixture comprising olefins, paraffins, and aromatics, wherein the third catalyst comprises at least one molecular sieve and at least one element selected from groups 2-14 of the Periodic Table;

d) conducting the third mixture away as reactor effluent.

2. The process of claim 1, wherein the first zone temperature is from 300° C. to 450° C., the second zone temperature is from 400° C. to 550° C., and the third zone is at a temperature greater than 500° C.

3. The process of claim 1, wherein the first catalyst in the first zone is prepared by steaming the first catalyst in the presence of at least 1 vol% water at a temperature of about 400° C. for at least 0.25 hours prior to executing step (a).

4. The process of claim 1, wherein the first catalyst and second catalyst are prepared by steaming the first and second catalyst in the presence of at least 1 vol% water at a temperature of about 400° C. for at least 0.25 hours prior to executing step (a).

5. The process of claim 1, wherein the at least one molecular sieve of the first and second catalyst comprises ZSM-5.

6. The process of claim 5, wherein the at least one element selected from groups 2-14 of the Periodic Table is one or more selected from the group consisting of Zn, Ga, or Ag.

7. The process of claim 1, where the reactor is operated at a pressure from 100 kPaa to 2500 kPaa and a weight hourly space velocity from 0.1 $hr^{-1}$ to 20 $hr^{-1}$.

8. The process of claim 1, wherein the second catalyst has at least >1 wt% more transition metal concentration than the first catalyst.

* * * * *